US012708439B2

(12) United States Patent
Maier

(10) Patent No.: US 12,708,439 B2
(45) Date of Patent: Aug. 18, 2026

(54) ELECTROSURGICAL SYSTEM AND METHOD FOR CHECKING THE ELECTRICAL CONNECTION BETWEEN A NEUTRAL ELECTRODE AND A PATIENT

(71) Applicant: Erbe Elektromedizin GmbH, Tuebingen (DE)

(72) Inventor: Philipp Maier, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 416 days.

(21) Appl. No.: 18/184,867

(22) Filed: Mar. 16, 2023

(65) Prior Publication Data

US 2023/0293230 A1 Sep. 21, 2023

(30) Foreign Application Priority Data

Mar. 17, 2022 (EP) .................................... 22162783

(51) Int. Cl.
*A61B 18/16* (2006.01)
*A61B 18/00* (2006.01)
*A61B 18/12* (2006.01)

(52) U.S. Cl.
CPC .......... *A61B 18/16* (2013.01); *A61B 18/1206* (2013.01); *A61B 2018/00178* (2013.01);
(Continued)

(58) Field of Classification Search
CPC . A61B 18/16; A61B 18/1206; A61B 18/1233; A61B 2018/00178;
(Continued)

(56) References Cited

U.S. PATENT DOCUMENTS 5,000,753 A * 3/1991 Hagen ...................... A61N 1/06 607/152
5,087,257 A 2/1992 Farin et al.
(Continued)

FOREIGN PATENT DOCUMENTS

CN 102215768 A 10/2011
CN 101912265 B 10/2014
(Continued)

OTHER PUBLICATIONS

Valentinuzzi, M. E., et al; "Bioelectrical Impedance Techniques In Medicine Part II: Monitoring Of Physiological Events By Impedance", Critical Reviews In Biomedical Engineering, CRC Press, Boca Raton, FL, Jan. 1, 1996; 114 pages.
(Continued)

*Primary Examiner* — Beverly M Flanagan
(74) *Attorney, Agent, or Firm* — Fitch, Even, Tabin & Flannery LLP

(57) ABSTRACT

An electrosurgical system includes a supply apparatus and a neutral electrode. A measurement signal is applied or impressed to the neutral electrode and the resulting impedance actual value ($Z_{ist}$) of the neutral electrode current circuit can be determined. The measurement signal (US, IS) is applied at different measurement frequencies (ω) and one impedance actual value ($Z_{ist}$) for each measurement frequency (ω) is determined. The impedance actual values characterize a frequency-dependent progress of the impedance and can be checked by a predefined frequency-dependent check criterion. It can thereby be recognized whether the conductive connection between the neutral electrode and the patient complies with the specifications defined by the check criterion. Particularly it is checked whether a sufficiently large area portion of the neutral electrode is conductively connected to the patient, so that excessive current
(Continued)

densities in the region of the neutral electrode inside the tissue of the patient can be avoided.

17 Claims, 6 Drawing Sheets

(52) U.S. Cl.
CPC ............... *A61B 2018/00875* (2013.01); *A61B 2018/128* (2013.01); *A61B 2018/167* (2013.01)

(58) Field of Classification Search
CPC .... A61B 2018/00875; A61B 2018/128; A61B 2018/167; A61B 2018/1253
USPC ...................................................... 606/35, 41
See application file for complete search history.

(56) References Cited

U.S. PATENT DOCUMENTS

| | | | | | |
|---|---|---|---|---|---|
| 5,928,159 | A | 7/1999 | Eggers et al. | | |
| 6,007,532 | A | 12/1999 | Netherly | | |
| 7,736,359 | B2 * | 6/2010 | McPherson | A61B 18/1233 | 606/35 |
| 11,744,492 | B2 * | 9/2023 | Hahn | A61B 5/14546 | 600/345 |
| 2008/0281309 | A1 * | 11/2008 | Dunning | A61B 18/16 | 606/32 |
| 2009/0281539 | A1 * | 11/2009 | Selig | A61B 18/16 | 606/41 |
| 2010/0280512 | A1 * | 11/2010 | Reick | B32B 37/18 | 606/41 |
| 2010/0331835 | A1 * | 12/2010 | Shilev | A61B 18/1233 | 606/41 |
| 2012/0232548 | A1 | 9/2012 | Behnke, II | | |
| 2012/0323236 | A1 * | 12/2012 | Hagg | A61B 18/1233 | 606/41 |
| 2015/0282725 | A1 | 10/2015 | Single | | |
| 2016/0059023 | A1 | 3/2016 | Freeman et al. | | |
| 2020/0069226 | A1 | 3/2020 | Hahn et al. | | |
| 2020/0245910 | A1 | 8/2020 | Mallas et al. | | |
| 2021/0068696 | A1 | 3/2021 | Kassegne et al. | | |
| 2023/0190364 | A1 * | 6/2023 | Curran | A61B 18/00 | 606/41 |

FOREIGN PATENT DOCUMENTS

| | | | |
|---|---|---|---|
| DE | 102016214704 | A1 | 2/2018 |
| DE | 102018114482 | A1 | 12/2019 |
| DE | 102019209333 | A1 | 12/2020 |
| EP | 0813387 | A1 | 12/1997 |
| EP | 1289415 | A1 | 3/2003 |
| EP | 2537479 | A1 | 12/2012 |
| EP | 3496638 | A1 | 6/2019 |
| RU | 2014 145 82313 | A | 6/2016 |
| WO | 01/87154 | A1 | 11/2001 |
| WO | 03/060462 | A2 | 7/2003 |

OTHER PUBLICATIONS

International Search Report for European Patent Application No. 22162783.9-1113 dated Aug. 30, 2022; 10 pages.

Federal Service for Intellectual Property of the Russian Federation; Office Action in corresponding Russian Patent Application No. 2023 105 651, dated Feb. 24, 2026; 13 pages.

China National Intellectual Property Administration; Office Action and Search Report in corresponding Chinese Patent Application No. 202310254380.0, dated Mar. 27, 2026, 18 pages.

Office Action for Japanese Application No. 2023-034477 dated Jun. 23, 2026.

* cited by examiner

ELECTROSURGICAL SYSTEM AND METHOD FOR CHECKING THE ELECTRICAL CONNECTION BETWEEN A NEUTRAL ELECTRODE AND A PATIENT

CROSS REFERENCE TO RELATED APPLICATION

This application claims the benefit of European Patent Application No. 22162783.9, filed Mar. 17, 2022, which is incorporated herein by reference in its entirety.

TECHNICAL FIELD

The invention refers to an electrosurgical system and a method for checking the electrical connection between a neutral electrode and a patient. The electrosurgical system can be particularly configured for carrying out the method. The electrosurgical system is particularly a system having a monopolar instrument and a neutral electrode that are connected or can be connected to a supply apparatus.

BACKGROUND

In electrosurgical instruments the electrical circuit from the supply apparatus to the operating electrode of the instruments and therefrom back to the supply apparatus has to be closed during treatment of a patient. For this purpose an additional electrode, that is denoted as neutral electrode, is attached to the patient in case of a monopolar instrument. Thus, the current can flow from the supply apparatus via the working electrode, the patient and the neutral electrode back to the supply apparatus.

The current density at the neutral electrode must not become too high in order to avoid endogenous burns during operation of the electrosurgical system. For this reason it is necessary that the provided conductive contact surface of the neutral electrode is attached to the patient with a sufficiently large area portion being in electrical connection at low resistance. A too small area portion of the contact surface that is electrically connected to the patient can make the current densities increase and thus cause endogenous burns in the tissue next to the neutral electrode. Thereby not only the initial correct attachment of the neutral electrode on the patient has to be considered, but the correct attachment of the neutral electrode on the patient has to be maintained during the entire use of the electrosurgical system.

EP 2 537 479 A1 describes the control of a medical apparatus depending on the neutral electrode impedance. The impedance is compared with a predefined threshold and the operation of the electrosurgical system or the treatment instrument respectively is only allowed, if the impedance of the neutral electrode is within a predefined range, e.g. has an amount of 140 Ohm at most.

SUMMARY

Such an impedance measurement with threshold comparison is insufficient. A too small area portion of the contact surface of the neutral electrode on the patient cannot be recognized in all of the cases by means of such an impedance measurement.

The invention is based on the finding that the impedance change of the neutral electrode depends on the location of the neutral electrode where the surface portions of the contact surface are that are detached from the patient and on where the locations of the surface areas of the contact surface are that are still electrically conductively connected with the patient. In the methods known up to present (EP 2 537 479 A1) the danger exists that not in all of the cases an electrically insufficient contact between the neutral electrode and the patient can be recognized.

Thus, it can be considered as one object of the present invention to provide an electrosurgical system and a method for checking the electrical connection between a neutral electrode and a patient in which an improved check of the electrically conductive connection between the neutral electrode and the patient is possible.

This object is solved by means of an electrosurgical system and method as described herein.

The electrosurgical system according to the invention comprises a supply apparatus having a neutral connection to which a neutral electrode is connected. The neutral electrode is configured to be electrically conductively connected with a patient. For this purpose the neutral electrode can be adhesively connected on the skin of the patient or can be attached otherwise.

A particularly periodically varying measurement signal can be applied to the neutral connection for the neutral electrode by means of the supply apparatus. The measurement signal can be an alternating voltage measurement signal or an alternating current measurement signal. The alternating voltage measurement signal causes a measurement current that flows through the neutral electrode. The alternating current measurement signal causes a measurement voltage that is applied to the neutral electrode. The measurement current or the measurement voltage can be measured at the neutral connection of the supply apparatus and based on the alternating voltage measurement signal and the measurement current or the alternating current measurement signal and the measurement voltage an impedance actual value can be determined for the neutral electrode.

In a preferred embodiment an alternating voltage measurement signal is used in form of a voltage source instead of an alternating current measurement signal in form of a current source for measurement of the impedance in order to not measure non-linear, voltage-dependent impedance portions.

According to the invention, the impedance actual value is not only determined at one single measurement frequency, but for multiple different measurement frequencies of the measurement signal (alternating voltage measurement signal or alternating current measurement signal). For this purpose the measurement frequency of the measurement signal is varied between multiple measurement frequencies and one impedance actual value is determined for each of the measurement frequencies respectively. The impedance actual value is thus frequency-dependent. In doing so, a frequency-dependent impedance progress can be at least approximately determined, for example.

The measurement frequency for the measurement signal can be preferably selected from a frequency range of 10 Hz to 1.0 MHz. For example, one impedance actual value for each measurement frequency can be determined respectively for minimum 10 or minimum 20 or minimum 50 different measurement frequencies. Preferably at least one measurement frequency can be selected from the range of 10 Hz up to 100 Hz. Further preferably at least one measurement frequency can be selected from the range of 100 kHz to 1.0 MHz. Two of the selected measurement frequencies can be equal to the limits of the entire possible frequency range, so that according to an example the lowest measurement frequency can be 10 Hz and the highest measurement frequency can be 1.0 MHz. In the indicated measurement frequency range starting with 10 Hz, ten measurement frequencies per order of magnitude having different amounts can be selected, for example. The frequency spacing between two measurement frequencies can be equal or can increase exponentially with the frequency.

The amplitude of the alternating voltage measurement signal is preferably smaller than 0.1 V. In an embodiment the amplitude of the alternating voltage measurement signal can be approximately 10 mV.

The impedance actual values can be checked based on a predefined frequency-dependent check criterion. Thus, the check criterion allows a frequency-dependent evaluation of the determined impedance actual value. For each measurement frequency an evaluation of the determined impedance actual value can be carried out. Particularly, thereby capacitive and ohmic influences on the impedance actual values can be more easily recognized and distinguished. For example, a frequency-dependent impedance desired range can be defined as check criterion within which the measured impedance actual values have to be. The impedance desired range can thereby have a linear or non-linear progress depending from the measurement frequency and is particularly non-constant.

It has turned out that due to the measurement and evaluation of the impedance of the neutral electrode at multiple measurement frequencies an improved evaluation of the electrical connection between the neutral electrode and the patient can be achieved. For example, insufficient electrical connections between the neutral electrode and the patient can be recognized independent from which spatial surface area portions of the neutral electrodes are not electrically conductively connected with a patient. Particularly an insufficient electrical contact between the neutral electrode and the patient can be recognized independent from the location at which or the spatial direction from which the neutral electrode detaches from the patient during the operation of the electrosurgical system.

The measurement of impedances at different measurement frequencies is indeed known per se, e.g. from the impedance spectroscopy. However, thereby the distinction of tissue types shall be facilitated that are treated by means of the electrosurgical system. Such a method is described in EP 1 289 415 A1, for example. By means of the instrument used for the treatment, a check signal is applied to the treated tissue at different frequencies and based on the measured impedance, the treated tissue is characterized in order to recognize different tissue types.

EP 0 813 387 A1 discloses an apparatus for the characterization and the treatment of tumors. Also here the impedance of the tissue treated by means of an instrument is used for distinction of different tissue types.

In the method known from WO 03/060462 A2 an electrical pulse is introduced into a tissue and its reflection is detected. Based on the reflection, healthy tissue shall be distinguished from maligned tissue in real time.

An electrosurgical system having a measurement unit is in addition described in EP 3 496 638 A1. There an impedance measurement of the treated tissue is carried out at different frequencies by means of a measurement device. By means of the measurement device a measurement signal can be applied to the tissue. A switching device serves to switch between a voltage for treatment of the tissue and the measurement signal. By means of the measurement signal the impedance of the tissue is determined at different frequencies.

Another method for determination of a local tissue type of body tissue and a respective electrosurgical system are described in DE 10 2019 209 333 A1. For tissue determination a measurement signal (alternating voltage or alternating current) is coupled into the tissue, wherein the frequency may vary. For example, based thereon an impedance spectrum can be detected and therefrom the tissue type can be derived.

In the current circuit between the supply apparatus, the instrument, the patient and the neutral electrode the impedance varies dependent on a multiplicity of parameters, so that a conclusion on the electrical contact between the neutral electrode and the patient is not possible. Different thereto the present invention allows an improved evaluation of the electrical connection between the neutral electrode and the patient compared with the prior art.

In a preferred embodiment the neutral electrode comprises multiple electrode sections, e.g. two or three, which are not directly electrically connected with one another. The electrode sections are thus not short-circuited. They can therefore have different electrical potentials. Inside the neutral electrode the electrode sections are, with regard to the occurring currents and voltages, electrically insulated from one another and an electrical connection exists preferably exclusively indirectly via the patient, if the neutral electrode is attached to the patient. For example, the neutral electrode can have an electrically conductive first electrode section and an electrically conductive second electrode section.

Preferably at least two of the present electrically conductive electrode sections are connected by means of a conductor with the neutral connection of the supply apparatus. For example, the first electrode section can be electrically connected via a first conductor and the second electrode section can be connected via a second conductor with the neutral connection. The two conductors are electrically insulated relative to each other for the occurring currents and voltages.

It is advantageous, if the first electrode section and the second electrode section have equal surface areas and/or the same geometry. In a preferred embodiment the two electrode sections are arranged with distance to one another. They can be electrically insulated from each other by means of an electrically non-conductive web of the neutral electrode.

In an embodiment the first electrode section and the second electrode section can be arranged on opposite sides of a reference plane and can be arranged symmetrically relative to the reference plane. The reference plane can extend along the web that separates the two electrode sections from one another.

Preferably the neutral electrode comprises an electrically conductive third electrode section. The third electrode section is electrically insulated relative to the first electrode section and the second electrode section for the occurring currents and voltages within the neutral electrode. An electrical connection between two or more electrode sections can be established exclusively indirectly, e.g. by means of an electrically conductive connection of two or more electrode sections with an electrically conductive structure, such as the patient, if the neutral electrode is attached to the patient.

The third electrode section can surround the first electrode section and the second electrode section. Preferably the third electrode section is curved and/or bent in multiple sections along its extension direction and is further preferably configured without interruptions. For example, it can have a U- or C-shaped extension. The third electrode section is preferably only open at one single location at which a connection area is present for electrical contacting of the first electrode section and the second electrode section with the first conductor or the second conductor respectively.

The surface area of the third electrode section can be smaller than the surface area of the first electrode section and/or the second electrode section. In a preferred embodiment the length of the third electrode section along its extension direction—preferably around the first electrode section and the second electrode section—has an amount that is larger about the factor 10 or 20 than the amount of its maximum width orthogonal to this extension direction (length).

As already explained above, the check criterion can be based on one or multiple predefined frequency-dependent impedance comparison values. For example, a frequency-dependent upper impedance limit value and/or a frequency-dependent lower impedance limit value can be predefined with which a determined impedance actual value is compared or the determined impedance actual values are compared. Based on this check it can be determined whether the neutral electrode abuts on the patient according to the provisions with sufficiently electrically conductive contact.

In a preferred embodiment the check criterion can be based on that a model impedance is predefined characterizing the neutral electrode. This model impedance can describe the dependency of the impedance actual values from multiple influence values or parameters. To these parameters also pertain the spatial dependency of the surface portions of the contact surface of the neutral electrode, that are connected with a patient in a low resistance manner or the surface area portions of the neutral electrodes that do not have an electrical connection to the patient at sufficiently low resistance. Thus, for example, a spatial direction can be considered from which the neutral electrode detaches from the patient starting from its edge.

Preferably the model impedance comprises a Warburg impedance and/or a constant phase element (CPE).

The Warburg impedance can provide multiple parameters for characterizing the behavior of the neutral electrode as part of the model impedance, e.g. a direct voltage resistance and a time constant. The direct voltage resistance and the time constant can be determined by simulation and/or empirically and depend on the respective configuration of the neutral electrode.

The constant phase element is an element that defines a constant phase shift as predefinable parameter, particularly in the range of 0° to −90° and can characterize a capacitive influence. Dependent on the provision of the phase shift defined by means of the selectable parameter, the constant phase element can characterize an exclusively ohmic resistance (phase shift 0°), an ideal capacitor (phase shift −90°) or a combination thereof.

In an embodiment the model impedance has a parallel connection, whereby the Warburg impedance and the constant phase element are connected parallel to one another.

In addition, the model impedance can comprise at least one resistor. In a preferred embodiment two resistors are present. One resistor is connected in series to the Warburg impedance inside the parallel connection, whereas the other resistor can be connected in series to the parallel connection. Thus, the model impedance can correspond to a Randles circuit.

By means of the model impedance multiple (e.g. five) parameters or variables can be provided that can be defined by means of simulation and/or measurement in order to describe the neutral electrode with regard to the frequency dependency of the impedance as well as the spatial arrangement of the area portions of the neutral electrode that abut against the patient in an electrically conductive manner.

Additionally or alternatively to a check criterion that is based on at least one frequency-dependent impedance comparison value, also a classification using at least one classifier can be carried out. Thereby the classifier can be directly applied on determined impedance actual values and/or on one or more surrogate parameters that have been determined based on the determined impedance actual values and/or the model impedance. Such surrogate parameters can be obtained, for example, in that all of the available variables or parameters are converted into one or multiple surrogate parameters by means of a method of dimensional reduction. Methods of dimensional reduction are known, e.g. in Form of the Principle Component Analysis (PCA) or by mathematical or statistical methods, such as t-Distributed Stochastic Neighbor Embedding, (t-SNE).

All known classifiers can be used as classifiers, e.g. one or more of the following classifiers: Bayes classifier, a support vector machine (SVM), an artificial neural network (for example a convolutional neural network (CNN), decision trees and/or a k-nearest-neighbor-algorithm (KNN).

For example, an artificial neural network can comprise two input neurons for each impedance actual value, i.e. for each predefined measurement frequency, so that the two dimensions (amount/phase or real part/imaginary part) of the respective impedance actual value can be supplied into the input layer of the artificial neural network. The artificial neural network can be trained based on training data in order to learn the different situations in which no sufficiently electrically conductive contact exists between the neutral electrode and the patient. The training data can be gained from actual operating data and/or from simulations and/or experiments in a laboratory.

In a preferred embodiment the electrosurgical system has a supply connection to which an electrosurgical instrument can be connected for treatment of tissue of a patient. The supply apparatus can apply an operating voltage and/or an operating current for the instrument to the supply connection. The operating voltage or an operating current can be preset by means of the supply apparatus depending on the surgical application, e.g. depending from whether tissue shall be coagulated, cut, ablated or fusioned by means of the instrument.

The instrument has an operating electrode. Based on the operating voltage, an electrode voltage can be applied to the operating electrode and/or based on the operating current an electrode current can flow through the operating electrode and further into the tissue to be treated. The operating voltage can be used as electrode voltage and/or the operating current can be used as electrode current.

In an embodiment the instrument is configured to request a respective operating voltage or a respective operating current at the supply connection. For this purpose an operating element of the instrument can be connected with the supply connection by means of the signal line. Additionally or alternatively, the current path between the supply connection and the operating electrode can be unblocked or interrupted or switched by means of an operating element. Thereby, as an option, it is possible to modify the provided operating voltage or the provided operating current within the electrical path from the supply connection to the operating electrode, e.g. by means of a converter circuit, so that the electrode voltage and/or the electrode current are different from the operating voltage or the operating current. Such a modification can also be used for creation of another type of operation external from the supply apparatus.

In an embodiment the electrosurgical system can be configured to apply the alternating voltage measurement signal only to the neutral connection and thus the neutral electrode, if no electrode voltage is applied to the operating electrode and/or no electrode current flow through the operating electrode into the tissue. Thus, the alternating voltage measurement signal can be applied in one or multiple periods between treatment periods to the neutral connection or the neutral electrode for determination of one or multiple impedance actual values. In doing so, the measurement current is not influenced by the operating voltage or the operating current and the determination of the impedance actual values is independent from the operating voltage and the operating current.

Additionally or alternatively to this, it is also possible to concurrently treat tissue by means of the operating electrode at least in phases (an electrode voltage is applied to the operating electrode and/or an operating current flows through the operating electrode) and to apply the alternating voltage measurement signal to the neutral connection or the neutral electrode. In the periods in which a treatment period and the application of the alternating voltage measurement signal overlap, the measurement frequency of the alternating voltage measurement signal can be selected different from the frequency of the operating voltage and/or the operating current and/or the electrode voltage and/or the electrode current. In doing so, it is guaranteed that the measurement current through the neutral electrode resulting from the alternating voltage measurement signal can be distinguished from the electrode current and a current flow caused therefrom—for example by evaluation of the frequency. Also in this case a sufficiently accurate determination of the impedance actual values is possible.

In a method for checking the electrical connection between the neutral electrode and the patient according to the present invention, the neutral electrode is attached to the patient in order to establish an electrically conductive connection to the patient. Subsequently, a measurement signal in form of an alternating voltage measurement signal or an alternating current measurement signal is applied or impressed to the neutral electrode—particularly via the neutral connection of the supply apparatus of an electrosurgical system according to any of the above embodiments. In doing so, a measurement current or a measurement voltage is created that can be measured. Thus, in turn an impedance actual value can be determined (ohms law) based on the applied alternating voltage measurement signal and the measurement current or the applied alternating current measurement signal and the measurement voltage. The measurement signal (alternating voltage measurement signal or alternating current measurement signal) is particularly produced subsequently at multiple different measurement frequencies and one impedance actual value respectively is determined for each selected and set measurement frequency. The impedance actual values obtained in this manner that extend over a frequency range defined by the measurement frequencies can be checked subsequently based on a predefined check criterion. This check provides a check result that indicates whether a sufficient electrical connection exists between the neutral electrode and the patient.

BRIEF DESCRIPTION OF THE DRAWINGS

Advantageous embodiments of the invention are derived from the dependent claims, the drawing and the description. In the following preferred embodiments are explained in detail based on the attached drawing. The drawings show:

DETAILED DESCRIPTION

Figure 1:
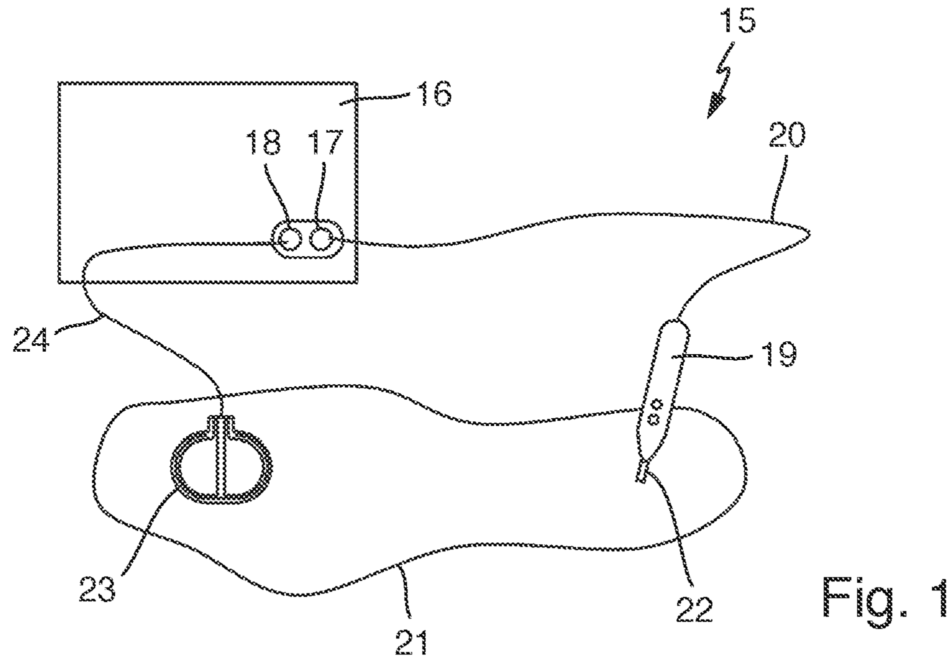
FIG. 1 a schematic block diagram-like illustration of an embodiment of an electrosurgical system comprising a supply apparatus, a neutral electrode and an instrument, FIG. 2 a schematic basic illustration of an embodiment of a neutral electrode, FIG. 3 a schematic basic illustration of transition resistances between electrode surfaces of the neutral electrode in FIG. 2, FIG. 4 exemplary principle changes of a total resistance of the neutral electrode according to FIGS. 2 and 3 dependent from an area portion of the total available contact area of the neutral electrode being in electrically conductive contact with the patient.

A basic illustration of an embodiment of an electrosurgical system 15 is shown in FIG. 1. The electrosurgical system 15 has a supply apparatus 16 having a supply connection 17 as well as a neutral connection 18. The supply connection 17 serves to electrically connect an instrument 19 with the supply apparatus 16. The electrical connection can be a unipolar or multipolar connection. Thus, the connection can be established via a unipolar or multipolar cable 20.

The instrument 19 is configured for electrosurgical treatment of biological tissue 21 of a patient. The tissue 21 is biological tissue of a human or animal body. For treatment of the tissue 21 instrument 19 has at least one or exactly one operating electrode 22. For treatment of tissue 21 an electrically conductive connection can be established between the operating electrode 22 and the tissue 21.

In the electrosurgical system 15 according to FIG. 1, instrument 19 is configured as monopolar instrument. A current circuit between the supply apparatus 16 operating electrode 22 of instrument 19 and again back to the supply apparatus 16 is not exclusively established via the instrument 19, but in addition via a separate electrode that is electrically conductively attached on the patient. This additional electrode can be denoted as neutral electrode 23. The neutral electrode 23 is electrically connected with the neutral connection 18 of supply apparatus 16 via a multi-pole cable 24 according to the example. For example, cable 24 has at least two leads or conductors and a first conductor 25 and a second conductor 26 in the illustrated embodiment (FIG. 2).

The supply apparatus 16 can apply an operating voltage UA (FIG. 9) for the operating electrode 22 to the supply connection 17. With an electrically conductive contact established between the operating electrode 22 and the tissue 21 an operating current IA flows through the operating electrode 22, further through the tissue 21 to the neutral electrode 23 and from there to the neutral connection 18 of the supply apparatus 16. The current circuit is closed.

Figure 9:
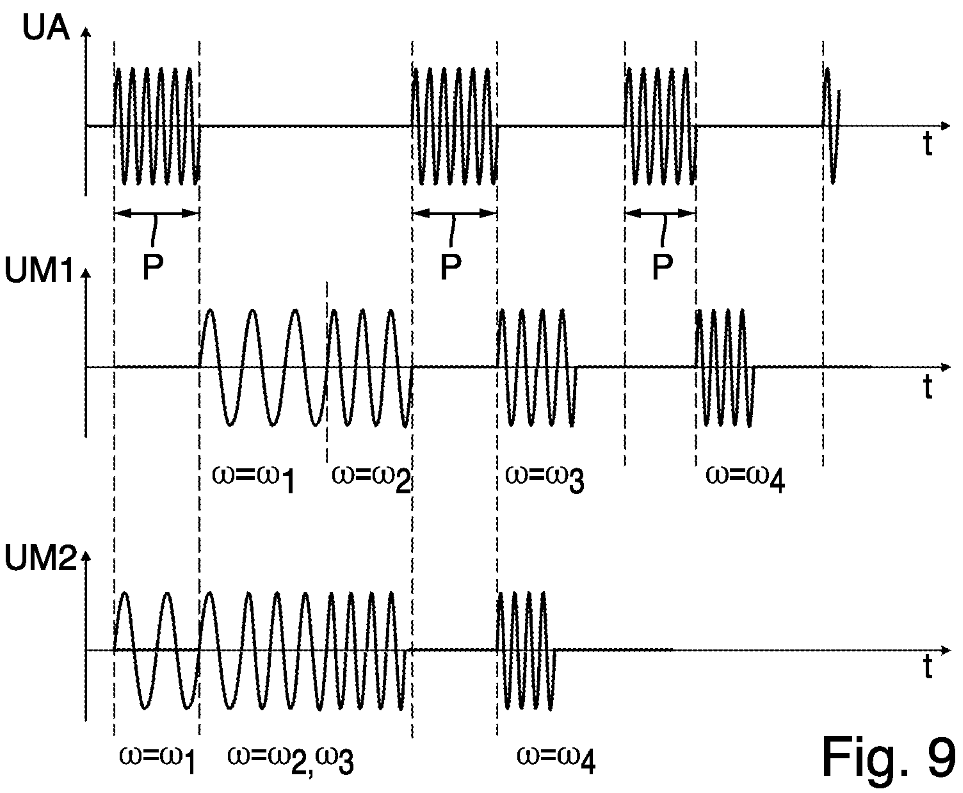

The operating voltage UA is a high-frequency voltage that is provided to the instrument 19 for treatment of tissue 21 and can be applied in the embodiment as electrode voltage to the operating electrode 22. As an option the operating voltage UA provided at the supply connection 17 can be converted by means of an inverter circuit or another modification circuit in a suitable electrode voltage. In the embodiment the operating voltage UA at the supply connection 17 can be requested by means of the instrument 19 via a signal line of cable 20. The operating voltage UA is then applied to the operating electrode 22 during treatment periods P at the supply connection 17, as schematically illustrated in FIG. 9.

Figure 2:
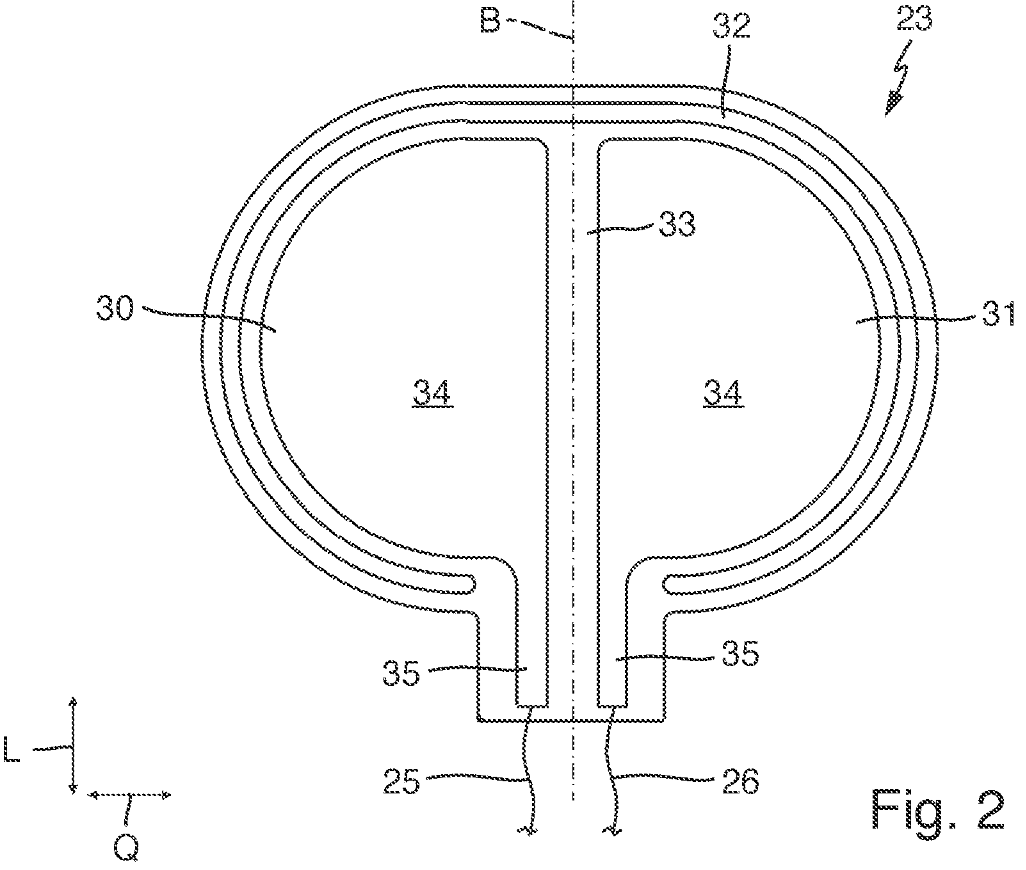

An embodiment of a neutral electrode 23 is illustrated in FIG. 2. The neutral electrode 23 has multiple electrically conductive electrode sections according to the example and in the preferred embodiment an electrically conductive first electrode section 30, an electrically conductive second electrode section 31 and an electrically conductive third electrode section 32. The electrode sections 30, 31, 32 are arranged with distance to one another and are electrically insulated from each other for the occurring voltages and currents so that each electrode section 30, 31, 32 can have a different electrical potential. In a condition attached to the patient the electrode sections 30, 31, 32 are exclusively indirectly electrically connected with one another via the patient. For example, the electrode sections 30, 31, 32 can be arranged with distance to one another on an electrically non-conductive carrier of the neutral electrode 23.

The electrode sections 30, 31, 32 are only configured as electrically conductive contact surface 34 on the side facing the patient and are on the respective other side electrically insulated by means of carrier material or other insulating material of the neutral electrode 23.

The first electrode section 30 and the second electrode section 31 have the same area and the same geometry. With reference to a reference plane B through the neutral electrode 23 the first electrode section 30 and the second electrode section 31 are arranged symmetrically. The reference plane B extends orthogonal to a transverse direction Q of neutral electrode 23. In a longitudinal direction L parallel to the reference plane B, an electrically non-conductive web 33 extends between the first electrode section 30 and the second electrode section 31.

The first electrode section 30 and the second electrode section 31 can comprise a substantially half-circular contact surface 34 respectively that is configured for abutment with the patient. The first electrode section 30 and the second electrode section 31 comprise a connection area 35 respectively that is realized by means of a strip-conductor-like extension of the respective contact surface 34. Starting from the contact surface 34 each connection area 35 can extend substantially in longitudinal direction L. In the connection area 35 the first electrode section 30 is electrically connected with the first conductor 25 and the second electrode section 31 is electrically connected with the second conductor 26.

The third electrode section 32 is not electrically connected with supply apparatus 16. Its electrical potential is thus not defined by means of supply apparatus 16.

The third electrode section 32 extends outside the connection area 35 completely around first electrode section 30 and second electrode section 31. The area of third electrode section 32 is preferably smaller than the area of the first electrode section 30 and the second electrode section 31. Along its extension direction or in circumferential direction around the first electrode section 30 and the second electrode section 31, the third electrode section 32 has a length, the absolute value of which is remarkably higher than the absolute value of its width with view orthogonal to its extension direction. The third electrode section 32 can thus be line-shaped or strip-conductor-shaped. Apart from the connection area 35, the third electrode section 32 is configured continuously without interruptions.

In the embodiment third electrode section 32 is the only electrode section that extends through reference plane B. It can have two arc-shaped and particularly circular arc-shaped end sections that are preferably connected with one another via a preferably straight connecting section.

Figure 3:
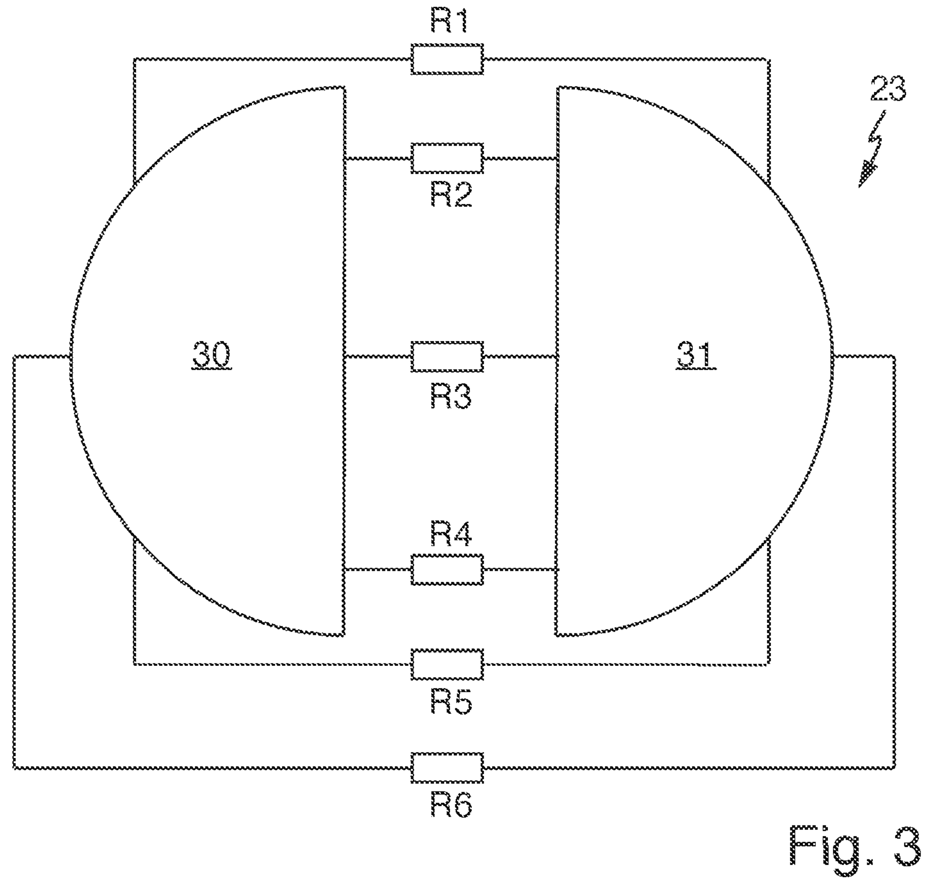

The neutral electrode shown in FIG. 2 has in an operating position in which it is attached to the patient different electrical transition resistances $R_k$ (k=1, 2, . . . , n) between first electrode section 30 and second electrode section 31 that vary depending on the spatial position (that is dependent on the position in longitudinal direction L and in transverse direction Q). The transition resistances $R_k$ (k=1, 2, . . . , n) vary dependent from the locations at the contact surfaces 34 or the electrode sections 30, 31 between which the transition resistance $R_k$ is measured. In the basic sketch according to FIG. 3 by way of example six transition resistances $R_1$ to $R_6$ are illustrated. The transition resistances (in the example: $R_1$, $R_5$ and $R_6$) that are effective between the edges of the electrode sections 30, 31, that do not adjoin web 33 and face away therefrom, are remarkably larger than the transition resistances (in the example: $R_2$, $R_3$ and $R_4$) between the edges of the electrode sections 30, 31 that directly adjoin web 33. Thereby the following can be approximately assumed:

$$R_1 \approx R_5 \approx R_6 \approx R_a \tag{1}$$

$$R_2 \approx R_3 \approx R_4 \approx R_i \tag{2}$$

$$R_a \gg R_i \tag{3}$$

Resulting from these transition resistances $R_a$ and $R_i$ having different magnitude, the total resistance $R_{ges}$ between first electrode section 30 and second electrode section 31 does not only change dependent from the area portion of the contact surface 34 that is in fact electrically conductively attached to the patient, when a reduction of the area of the contact surface 34 occurs, but also dependent from where this area portion is located on the neutral electrode 23—that is, for example, depending from whether the neutral electrode has detached from the patient in longitudinal direction L or in transverse direction Q.

Figure 4:
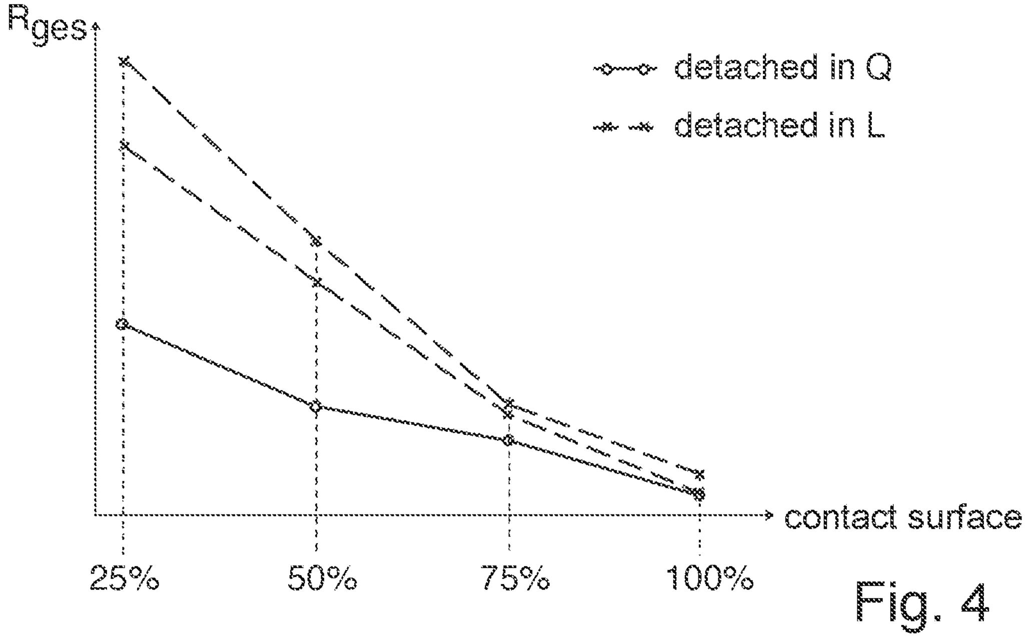

In FIG. 4, only by way of example and in schematic manner, measurements are illustrated for a detachment of neutral electrode 23 in transverse direction Q (continuous line in FIG. 4) and in longitudinal direction L (dashed lines in FIG. 4). It is apparent therefrom that the total resistance $R_{ges}$ between first electrode section 30 and second electrode section 31 does not readily allow the conclusion on the area content of the contact surface 34 that is in fact electrically conductively connected with the patient. As total resistance $R_{ges}$ here the real part of the impedance of the electrical connection between the first conductor 25 and the second conductor 26 via tissue 21 is determined.

Figure 7:
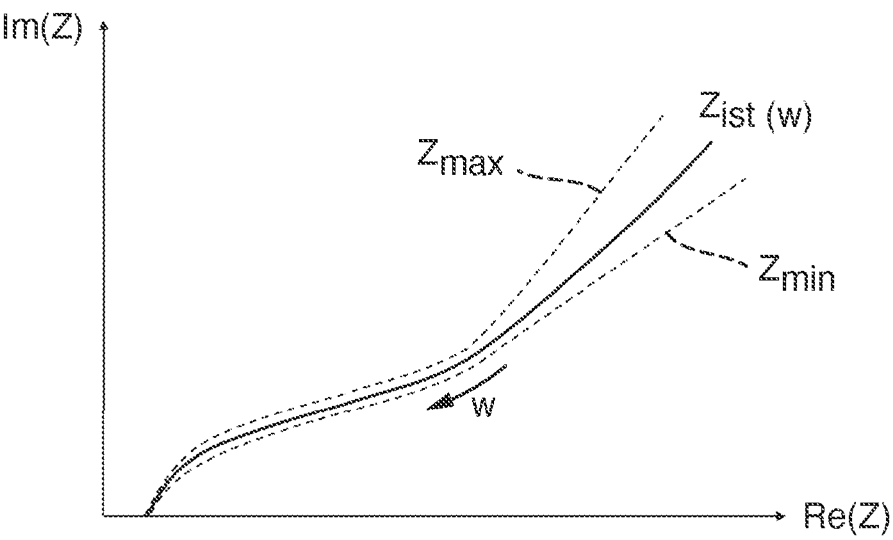

According to the invention, an improved monitoring of the electrical connection between neutral electrode 23 and the patient shall be achieved. For this reason it is provided to determine the impedance Z between first electrode section 30 and second electrode section 31 by means of an alternating voltage measurement signal US or an alternating current measurement signal IS at different measurement frequencies w. For example, therefrom a frequency-dependent impedance progress of multiple impedance actual values $Z_{ist}$ can be determined. In FIG. 7 the impedance actual values $Z_{ist}$, the real part Re(Z) and the imaginary part Im(Z) of the impedance actual values $Z_{ist}$, are illustrated dependent from the measurement frequency ω as Nyquist diagram (measurement frequency ω increases starting from the intersection with the abscissa).

As also apparent from FIG. 7, the frequency-dependent impedance progress or individual impedance actual values $Z_{ist}$ can be checked whether it is or they are within an allowable range. Based on this check criterion, it can be decided whether a sufficiently good electrical contact is present between the neutral electrode 23 and the patient and thus a sufficiently large area portion of the available contact surface 34 of the electrode sections 30, 31 abuts electrically conductively on the patient. In the embodiment according to FIG. 7, the check criterion is thus the comparison of the measured impedance actual values $Z_{ist}$ with one or more frequency-dependent impedance comparison values. For example, as impedance comparison value an upper impedance limit value $Z_{max}$ and/or a lower impedance limit value $Z_{min}$ can be predefined. If it is determined that one or more of the measured impedance actual values $Z_{ist}$ are not within the predefined range, a non-correct electrical connection between neutral electrode 23 and the patient can be concluded.

By evaluation of the impedance Z of neutral electrode current circuit, that is the electrical connection between first electrode section 30 and second electrode section 31 or first conductor 25 and second conductor 26 respectively, by using an alternating voltage measurement signal US or an alternating current measurement signal IS at different measurement frequencies w, it can be more accurately determined independent from the spatial position on the neutral electrode 23 whether neutral electrode 23 is in tight abutment against the patient with a sufficiently large area portion of its at least one contact surface 34 and therefore the electrical connection corresponds to the requirements. In the evaluation according to the invention it does not play any role whether neutral electrode 23 detaches in longitudinal direction L, in transverse direction Q or obliquely to these directions from the patient, for example. In all circumstances the quality of the electrical connection can be evaluated with sufficient accuracy.

Figure 5:
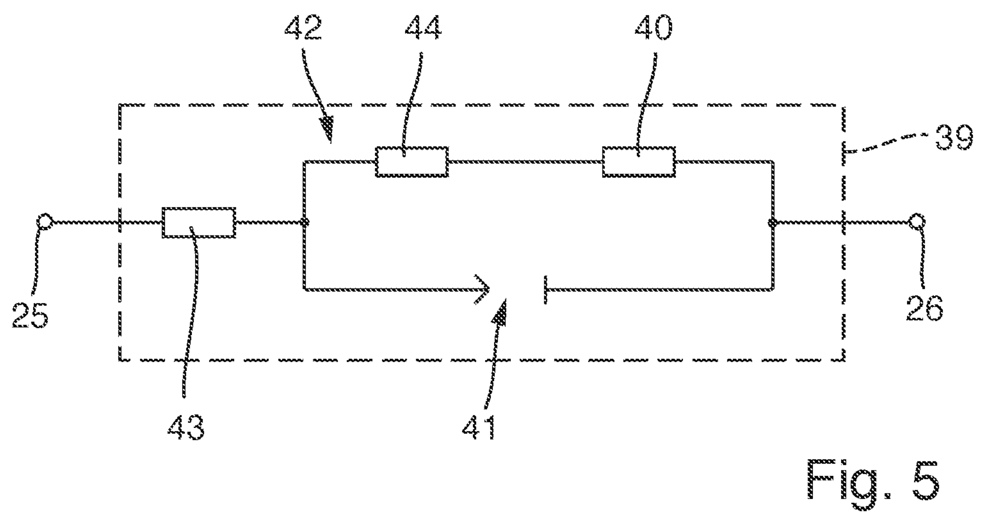
FIG. 5 a block diagram of a model impedance that characterizes the neutral electrode according to FIGS. 1 and 2, FIG. 6 a block diagram of the embodiment of the electrosurgical system according to FIG. 1, FIG. 7 an exemplary impedance progress based on multiple determined impedance actual values of the neutral electrode according to FIGS. 1 and 2, FIG. 8 schematically and only exemplarily illustrated fields that define the area portion of the available contact area, which is electrically conductively connected to the patient dependent from two principal components, FIG. 9 exemplary time-dependent progresses of an operating voltage and multiple possible alternating voltage measurement signals, FIG. 10 spectra of an operating current and a measurement current illustrated in a highly schematic manner and FIG. 11 a flow diagram of an embodiment of a method according to the invention.
Figure 6:
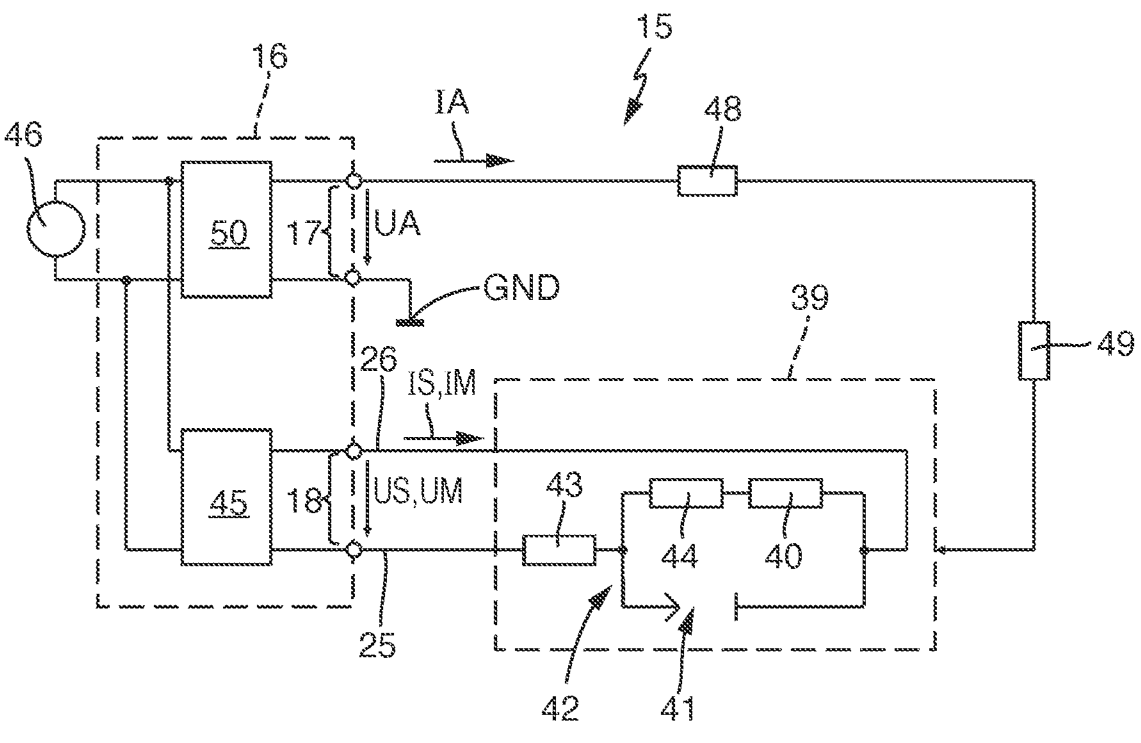

The invention is based on the finding that the impedance of the neutral electrode current circuit between first electrode section 30 and second electrode section 31 can be characterized by a model impedance 39 that is illustrated in FIGS. 5 and 6 in the form of a block diagram. The model impedance 39 comprises a Warburg impedance 40 according to the example. The Warburg impedance has a frequency-dependent impedance value W(ω):

$$W(\omega) = \frac{A_W}{\sqrt{\omega}} + \frac{A_W}{j\sqrt{\omega}} \tag{4}$$

wherein $A_W$ is the Warburg coefficient of the Warburg impedance 40 and ω is the angular frequency. The Warburg coefficient $A_W$ can be determined by means of measurement and/or simulation and can particularly depend on the dimension and/or geometry of neutral electrode 23.

In addition to the Warburg impedance 40, the model impedance 39 comprises a constant phase element 41 (CPE). The constant phase element 41 is a component that comprises a phase shift in a range of 0° to −90°. The constant phase element 41 can thus correspond to an ideal capacitor, an ohmic resistor or a combination thereof.

As illustrated in FIGS. 5 and 6, model impedance 39 comprises a parallel connection 42 and a first resistor 43 in series to the parallel connection 42. Within the parallel connection 42 the constant phase element 41 is connected in parallel to the Warburg impedance 40. Within the parallel connection a second resistor 44 can be connected in series to the Warburg impedance 40.

In the embodiment the model impedance 39, therefore, corresponds to a Randles circuit.

The model impedance 39 maps the behavior of neutral electrode 23 with sufficiently good approximation or accuracy.

For measurement of the impedance actual value $Z_{ist}$ the measurement signal (alternating voltage measurement signal US or alternating current measurement signal IS) is applied to or impressed at neutral connection 18 of supply apparatus 16 and supplied via cable 24 to the neutral electrode 23. The measurement signal US, IS is in this manner effective between first conductor 25 and second conductor 26 and thus between first electrode section 30 and second electrode section 31 of neutral electrode 23. Via neutral electrode 23 attached to the patient a current circuit between first electrode section 30 and second electrode section 31 is closed. Due to the alternating voltage measurement signal US, a measurement current IM flows through neutral electrode 23 or the alternating current measurement signal IS produces a measurement voltage UM over neutral connection 18. This measurement current IM or this measurement voltage UM can be detected in the supply apparatus 16, e.g. in a measurement unit 45 of supply apparatus 16 (FIG. 6). Based on the alternating voltage measurement signal US and the measurement current IM or based on the alternating current measurement signal IS and the measurement voltage UM, the impedance or the respective impedance actual value $Z_{ist}$ can be determined for the respectively actually set measurement frequency ω of the measurement signal US, IS.

As also illustrated in FIG. 6, supply apparatus 16 can be connected to an external energy supply, e.g. a grid voltage source 46. The measurement unit can be configured to produce the measurement signal US, IS from the supply voltage of the grid voltage source 46.

In the equivalent circuit according to FIG. 6, the impedance formed by instrument 19, operating electrode 22 and the transition from operating electrode 22 to the tissue 21 is illustrated by a first impedance 48. In series thereto a second impedance 49 represents the impedance from the contact location of operating electrode 22 with the tissue 21 to the neutral electrode 23 and the transition impedance between tissue 21 and neutral electrode 23.

As already explained, an operating voltage UA and/or an operating current IA for the instrument 19 is provided at supply connection 17. In the example illustrated in FIG. 6 the operating voltage UA is applied as electrode voltage to the operating electrode 22. The operating voltage UA can be provided by means of an inverter circuit 50 of supply apparatus 16, e.g. from the supply voltage of grid voltage source 46. Additionally or alternatively, it is also possible to arrange an inverter circuit in the instrument 19 or at another suitable location between supply connection 17 and operating electrode 22 in order to produce an electrode voltage based on the operating voltage UA that is suitable for the respective treatment.

The operating voltage UA corresponds to a potential difference between an operating potential and a reference potential, e.g. ground GND.

Schematically and exemplarily time-dependent progresses for the operating voltage UA as well as the measurement signal US, IS are illustrated in FIG. 9, wherein for sake of distinction a first measurement signal M1 and a second measurement signal M2 are introduced in FIG. 9. This distinction is only for sake of clarity in order to be able to better distinguish the possibilities from each other described in the following.

The measurement signal US, IS that is denoted as first measurement signal M1 here, is only applied to the neutral connection 17 or neutral electrode 23, if no treatment of tissue 21 by means of operating electrode 22 is carried out. The first measurement signal M1 is thus applied outside treatment periods P. In doing so, it is guaranteed that no mutual influence between operating voltage UA or operating current IA on one hand and first measurement signal M1 or a measurement current resulting therefrom exists.

For the first measurement signal M1 it can be seen in FIG. 9 that in a time period between two subsequent treatment periods P the measurement frequency ω can be constant or can also be modified. In the illustrated example in the considered time period, four different measurement frequencies $\omega_1$, $\omega_2$, $\omega_3$ and $\omega_4$ of first measurement signal M1 are illustrated. The number of used measurement frequencies ω can vary and can be selected depending on the application. The used measurement frequencies are selected from a frequency range of 10 Hz to 1.0 MHz.

The amplitude of the alternating voltage measurement signal US (peak or maximum value) is particularly smaller than 0.1 V or smaller than 50 mV. In the embodiment an amplitude of 10 mV is used. The amplitude of an alternating current measurement signal IS (peak or maximum value) is particularly lower than 1.0 mA or lower than 100 μA.

The time duration or number of periods during which the measurement signal US, IS is applied with unchanged measurement frequency ω may vary. This time duration has to be only long enough in order to detect the measurement current IM resulting therefrom or the measurement voltage UM resulting therefrom, in order that the impedance actual value $Z_{ist}$ can be determined from the applied alternating voltage measurement signal US and the measurement current IM according to ohms law.

Additionally or alternatively, the measurement signal US, IS can be applied at least in time sections during one or more treatment periods P to neutral connection 18 or neutral electrode 23, which is illustrated in FIG. 9 by measurement signal US, IS denoted as second measurement signal M2. In this case, measurement frequency ω that is used during treatment period P is selected sufficiently different from operating frequency of operating voltage UA and/or operating current IA. Due to this measure, the alternating current measurement signal IS or the resulting measurement current IM and the operating current IA can be distinguished so that the determination of the impedance actual value $Z_{ist}$ can be carried out with sufficient accuracy.

Apart therefrom, the same applies for the second measurement signal M2 as for the first measurement signal M1.

Figure 10:
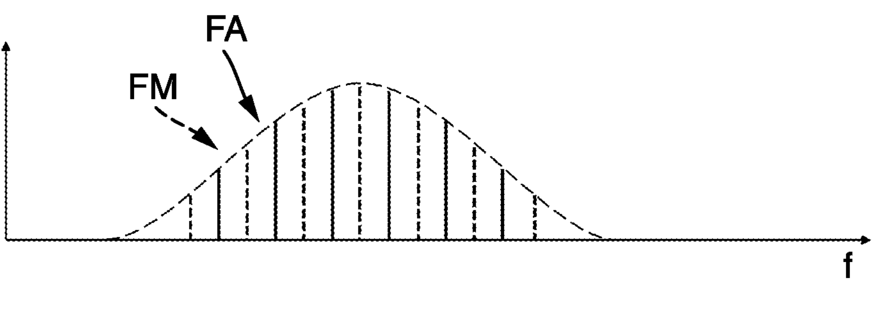

Additionally or alternatively to the evaluation in the time domain, also an evaluation in the frequency domain can be carried out. In FIG. 10 the spectrum FA of operating current IA is highly schematically illustrated with continuous lines and the spectrum FM of measurement current IM is highly simplified illustrated by the spectral lines shown in dashed lines. In the time domain the operating voltage UA and the alternating voltage measurement signal US and/or the operating current IA and the alternating current measurement signal IS or the measurement current IM can be superimposed. Thereby the signal progress of measurement signal US, IS in the time domain can be selected, so that the spectral lines of spectrum FM of alternating current measurement signal IS or measurement current IM are located adjacent to the spectral lines of spectrum FA of operating current IA, so that in the frequency domain a signal separation is possible and thus the impedance actual values can be determined substantially uninfluenced from the operating voltage UA or the operating current IA.

As explained above, the determined impedance actual values $Z_{ist}$ can be checked by means of preset impedance comparison values. Additionally or alternatively, also other check criterions or check methods can be used. For example, classifiers can be applied on the impedance actual values in order to determine therefrom the quality of the electrical connection (e.g. the portion of the available contact surfaces 34 that is in fact electrically conductively attached to the patient). For this purpose classifiers can be used, such as the Bayes classifier, an SVM (Support Vector Machine), an artificial neural network, a decision tree or other mathematical or statistical methods.

For example, the imaginary part Im(Z) and the real part Re(Z) of the impedance actual value $Z_{ist}$ or alternatively absolute value and phase of the impedance actual value $Z_{ist}$ can be submitted to an artificial neural network as input neurons for each defined measurement frequency ω within the entire frequency range (e.g. from 10 Hz to 1 MHz). For each defined measurement frequency thereby two input neurons of the neural network are derived. The artificial neural network can be trained by means of training data and thereupon recognize non-allowable deficient electrical connections between neutral electrode 23 and the patient.

The named classifiers can also be applied on pre-processed values or surrogate parameters that are derived, for example, from one or more measured impedance actual values $Z_{ist}$ and/or the available parameters of the model impedance 39. For example, from the model impedance used here multiple variables or parameters result that define the model impedance 39. In the embodiment according to FIG. 5, this can be five parameters, namely the absolute values of the resistors 43, 44, the phase position of constant phase element 41, the direct current resistance of Warburg impedance 40 as well as the time constant of Warburg impedance 40. By means of an optional dimension reduction, the number of parameters can be reduced on which the classifiers are applied.

Only by way of example FIG. 6 illustrates that classifiers are applied on two surrogate parameters, namely a first principle component HK1 and a second principle component HK2 that are determined based on the parameters of model impedance 39 by means of a principle component analysis (PCA). The number of remaining surrogate parameters is lower than the number of parameters of model impedance 39 and can also be larger or lower than two different to the illustration in FIG. 8.

Figure 8:
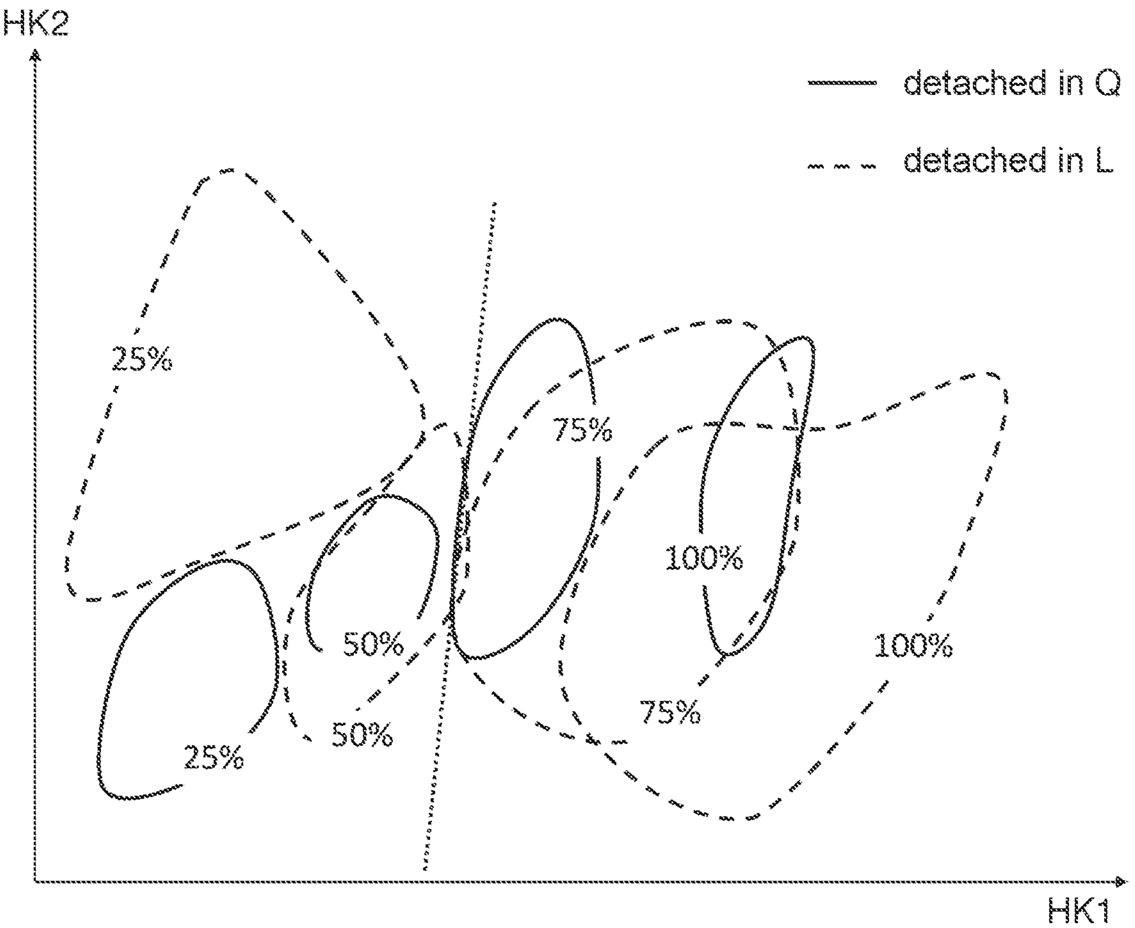

By way of example, fields are illustrated in FIG. 8 that indicate the percentage portion of contact surfaces 34 that are in fact electrically conductively connected with the patient. Therefrom by means of the application of classifiers, a sufficient electrical connection as well as an insufficient electrical connection between neutral electrode 23 and the patient can be determined.

Figure 11:
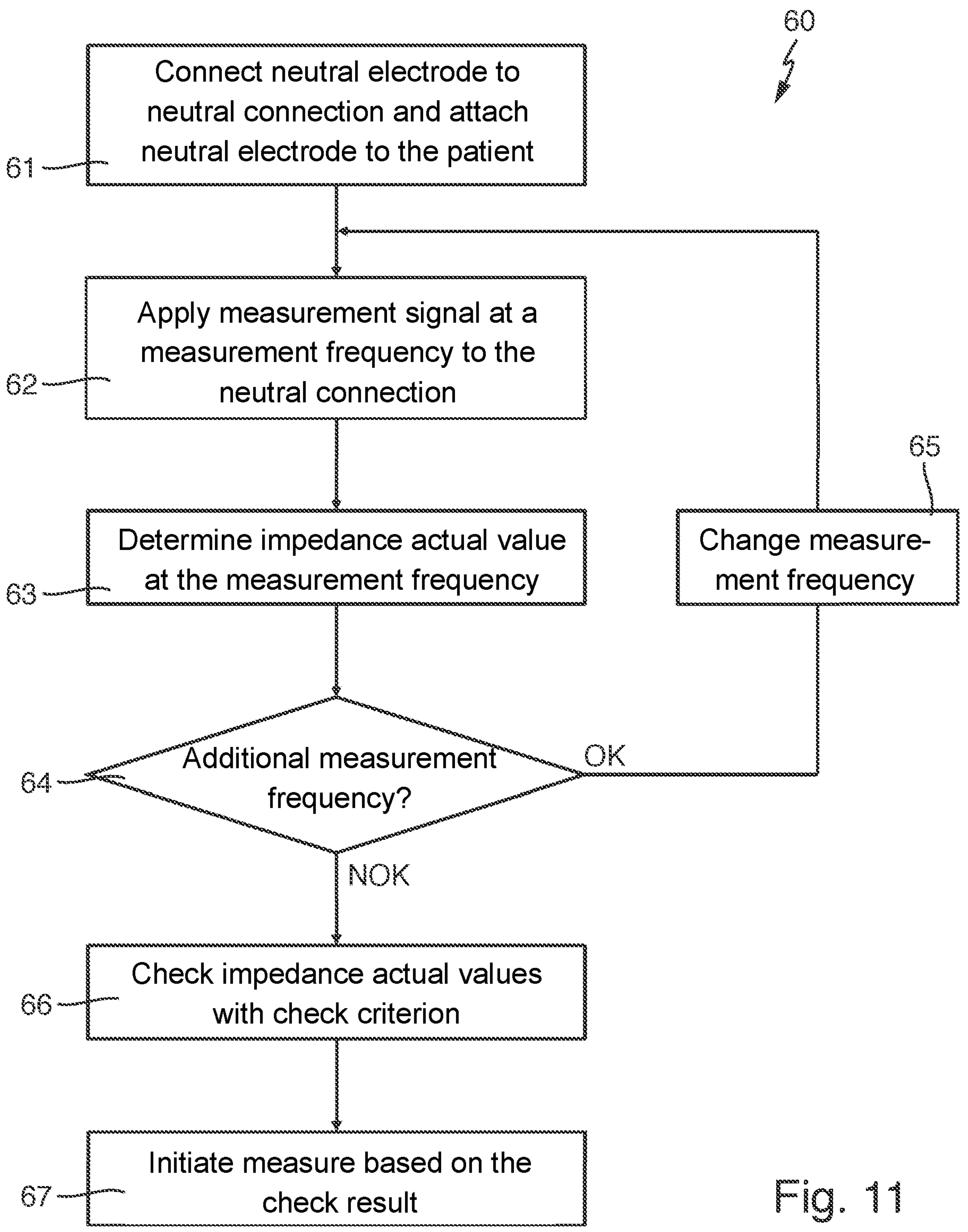

In FIG. 11 flow diagram of an embodiment of a method 60 is illustrated by means of which an electrical connection between a neutral electrode 23 and a patient can be checked.

In a first method step 61 neutral electrode 23 is connected to neutral connection 18 and is attached to the patient.

In second method step 62 a first measurement frequency is selected and a measurement signal US, IS is applied to the neutral connection 18 at the selected measurement frequency. The measurement current IM resulting therefrom or the measurement voltage UM resulting therefrom is detected, so that a first impedance actual value $Z_{ist}$ can be determined for the first measurement frequency (third step 63).

In a fourth method step 64 it is checked whether the impedance value determination shall be carried out for additional measurement frequencies w. For example, the impedance actual value can be determined for minimum ten measurement frequencies, minimum 20 measurement frequencies or more measurement frequencies. If an impedance actual value determination has not been carried out for all defined measurement frequencies (branch OK from the fourth method step 64), an additional measurement frequency is selected that is different from the measurement frequency or the measurement frequencies at which the impedance actual value has been determined so far. Following fifth method step 65 the method is continued in second method step 62.

Otherwise (branch NOK from fourth method step 64) the method is continued in a sixth method step 66.

In sixth method step 66 the impedance actual values $Z_{ist}$ determined at the different measurement frequencies ω are compared with the preset check criterion. For example, the check criterion can comprise a comparison with multiple preset frequency-dependent impedance comparison values. In addition or as an alternative, the use of one or multiple classifiers on the determined impedance actual values and/or parameters derived therefrom can be comprised.

The check result determined in the sixth method step 66 indicates whether the electrically conductive connection between neutral electrode 23 and the patient corresponds to the specifications or is insufficient so that unallowed high current densities in the range of the neutral electrode 23 could result therefrom inside tissue 21. This could in turn result in endogenous burns inside tissue 21.

In a seventh method step 67 a measure is initiated depending on the check result. For example, a notification can be output to an operating person—for example via an interface on supply apparatus 16—whether the electrical connection between neutral electrode 23 and the patient complies with the specifications. The notification can also contain information about the quality of the electrical connection and can be, for example, characteristic for the portion of the total available contact surfaces 34 that are electrically conductively connected to the patient.

If the electrical contact between neutral electrode 23 and the patient is deficient so that the danger of burns exists in the seventh method step 67, the operation of instrument 19 can be stopped, so that no further operating current IA can flow via operating electrode into tissue 21. For example, the production and application of operating voltage UA or operating current IA to supply connection 17 can be blocked.

The invention refers to an electrosurgical system 15 and a method 60 that can be used during operation of the electrosurgical system 15. The electrosurgical system 15 has a supply apparatus 16 as well as a neutral electrode 23 connected thereto. An alternating voltage measurement signal US can be applied to the neutral electrode 23 or an alternating current measurement signal IS flowing into the neutral electrode 23 can be impressed and the impedance actual value $Z_{ist}$ of the neutral electrode current circuit resulting therefrom can be determined. The measurement signal (alternating voltage measurement signal US or alternating current measurement signal IS) is applied or impressed at multiple different measurement frequencies ω and one impedance actual value $Z_{ist}$ is determined in each case for the respective measurement frequency ω. The impedance actual values obtained therefrom characterize a frequency-dependent progress of the impedance and can be checked with a predefined frequency-dependent check criterion. Based on the check it is determined whether the electrically conductive connection between neutral electrode 23 and the patient complies with the specifications defined by the check criterion. It is particularly checked whether a sufficiently large area portion of the neutral electrode 23 is electrically conductively connected to the patient so that too high current densities in the range of the neutral electrode 23 inside tissue 21 of the patient can be avoided.

LIST OF REFERENCE SIGNS

15 electrosurgical system
16 supply apparatus
17 supply connection
18 neutral connection
19 instrument
20 cable for instrument
21 tissue
22 operating electrode
23 neutral electrode
24 cable for neutral electrode
25 first conductor
26 second conductor
30 first electrode section
31 second electrode section
32 third electrode section
33 web
34 contact surface
35 connection area
39 model impedance
40 Warburg impedance
41 constant phase element
42 parallel connection
43 first resistor
44 second resistor
45 measurement unit
46 grid voltage source
48 first impedance
49 second impedance
50 inverter circuit
60 method
61 first method step
62 second method step
63 third method step
64 fourth method step
65 fifth method step
66 sixth method step
67 seventh method step
ω measurement frequency
$A_W$ Warburg coefficient of Warburg impedance
B reference plane
GND ground HK1 first main component
HK2 second main component
IM measurement current
IS alternating current measurement signal
L longitudinal direction
M1 first measurement signal
M2 second measurement signal
P treatment period
Q transverse direction
UA operating voltage
UM measurement voltage
US alternating voltage measurement signal
Z impedance
$Z_{ist}$ impedance actual value
$Z_{max}$ impedance upper limit value
$Z_{min}$ impedance lower limit value

The invention claimed is:

1. An electrosurgical system (15), comprising:
a supply apparatus (16) having a neutral connection (18); and
a neutral electrode (23) connected to the neutral connection (18) that is configured to be electrically conductively connected to a patient via at least one contact surface (34) thereof;
wherein the supply apparatus (16) is configured to provide a measurement signal (US, IS) solely to the neutral connection (18) at multiple different measurement frequencies (ω) at different times and to determine an impedance actual value ($Z_{ist}(\omega)$) of the neutral electrode (23) for individual ones of the multiple different measurement frequencies and to check the determined impedance actual values ($Z_{ist}(\omega)$) based on a predefined frequency-dependent check criterion;
wherein the predefined frequency-dependent check criterion is based on a frequency-dependent model impedance (39);
wherein the frequency-dependent model impedance (39) provides multiple parameters to characterize the neutral electrode (23) including a spatial dependency of surface portions of the at least one contact surface (34) of the neutral electrode (23) that are electrically connected to the patient with sufficiently low resistance or that do not have an electrical connection to the patient with sufficiently low resistance.

2. The electrosurgical system according to claim 1, wherein the neutral electrode (23) comprises an electrically conductive first electrode section (30) and an electrically conductive second electrode section (31), wherein electrical potentials of the electrically conductive first and second electrode sections (30, 31) are separated from one another.

3. The electrosurgical system according to claim 2, wherein the first electrode section (30) is electrically connected with the neutral connection (18) via a first conductor (25) and the second electrode section (31) is electrically connected with the neutral connection (18) via a second conductor (26).

4. The electrosurgical system according to claim 2, wherein the first electrode section (30) and the second electrode section (31) comprise at least one of areas of equal size and identical geometries.

5. The electrosurgical system according to claim 2, wherein the first electrode section (30) and the second electrode section (31) are arranged at a distance with respect to one another and symmetrically with respect to a reference plane (B) that extends through the neutral electrode (23).

6. The electrosurgical system according to claim 2, wherein the neutral electrode (23) comprises an electrically conductive third electrode section (32), wherein an electrical potential of the third electrode section (32) is separated from the electrical potentials of the first electrode section (30) and the second electrode section (31).

7. The electrosurgical system according to claim 6, wherein the third electrode section (32) surrounds the first electrode section (30) and the second electrode section (31).

8. The electrosurgical system according to claim 1, wherein the predefined frequency-dependent check criterion is based on at least one predefined frequency-dependent impedance comparison value $Z_{max}(\omega)$, $Z_{min}(\omega)$).

9. The electrosurgical system according to claim 1, wherein the frequency-dependent model impedance (39) comprises a Warburg impedance (40).

10. The electrosurgical system according to claim 9, wherein the frequency-dependent model impedance (39) comprises a parallel connection (42) in which the Warburg impedance (40) and a constant phase element (41) are connected in parallel to one another.

11. The electrosurgical system according to claim 1, wherein the supply apparatus (16) comprises a supply connection (17) and an instrument (19) having an operating electrode (22), wherein the instrument (19) is electrically connected to the supply connection (17), wherein at least one of the supply apparatus (16) and the instrument (19) are configured to supply at least one of an operating voltage (UA) and an operating current (IA) to the operating electrode (22).

12. The electrosurgical system according to claim 11, wherein the supply apparatus (16) is configured to apply the measurement signal (US, IS) to the neutral connection (18) only if no operating voltage (UA) and no operating current (IA) are supplied to the operating electrode (22).

13. The electrosurgical system according to claim 11, wherein the supply apparatus (16) is configured to set a measurement frequency (ω) of the multiple different measurement frequencies of the measurement signal (US, IS) differently compared to at least one of an operating frequency of the operating voltage (UA) and the operating current (IA), if the measurement signal (US, IS) is provided to the neutral connection (18) while the operating electrode (22) is supplied with at least one of an operating voltage (UA) and an operating current (IA).

14. A method for checking an electrical connection between a neutral electrode (23) and a patient, wherein the method comprises the following steps:
attaching the neutral electrode (23) via at least one contact surface (34) thereof to the patient so that an electrically conductive connection exists between the neutral electrode (23) and the patient;
applying a measurement signal (US, IS) respectively at multiple different measurement frequencies (ω) solely to the neutral electrode (23) at different times;
determining an impedance actual value ($Z_{ist}(\omega)$) for individual measurement frequencies (ω) of the multiple different measurement frequencies (ω) of the measurement signal (US, IS);
checking the determined impedance actual values ($Z_{ist}(\omega)$) based on a predefined check criterion, and
initiating a measure depending on a result of the checking of the determined impedance actual values ($Z_{ist}(\omega)$);
wherein the predefined check criterion is based on a frequency-dependent model impedance (39);
wherein the frequency-dependent model impedance (39) provides multiple parameters to characterize the neutral electrode (23) including a spatial dependency of surface portions of the at least one contact surface (34) of the neutral electrode (23) that are electrically connected to the patient with sufficiently low resistance or that do not have an electrical connection to the patient with sufficiently low resistance.

15. The electrosurgical system according to claim 2, wherein the supply apparatus (16) is configured to determine the impedance actual value ($Z_{ist}(\omega)$) of the neutral electrode (23) between the electrically conductive first electrode section (30) and the electrically conductive second electrode section (31) for individual ones of the multiple different measurement frequencies at different times and to determine a frequency-dependent impedance value progression from the impedance actual values for the individual ones of the multiple different measurement frequencies.

16. The method of claim 14, wherein applying a measurement signal (US, IS) respectively at multiple different measurement frequencies ($\omega$) to the neutral electrode (23) comprises varying the measurement frequency of the measurement signal over a period of time, wherein one impedance actual value is determined for each of the measurement frequencies at different times.

17. The method of claim 16, further comprising determining a frequency-dependent impedance progression based on the impedance actual values determined for each of the measurement frequencies at the different times.

* * * * *